(12) United States Patent
Leidner

(10) Patent No.: US 9,513,146 B2
(45) Date of Patent: Dec. 6, 2016

(54) INSERTION MOUNT DEVICE

(71) Applicant: Hach Company, Loveland, CO (US)

(72) Inventor: Ralf Leidner, Fort Collins, CO (US)

(73) Assignee: Hach Company, Loveland, CO (US)

( * ) Notice: Subject to any disclaimer, the term of this patent is extended or adjusted under 35 U.S.C. 154(b) by 243 days.

(21) Appl. No.: 14/499,704

(22) Filed: Sep. 29, 2014

(65) Prior Publication Data

US 2015/0090054 A1 Apr. 2, 2015

Related U.S. Application Data

(60) Provisional application No. 61/885,482, filed on Oct. 1, 2013.

(51) Int. Cl.
*G01D 11/30* (2006.01)
*G01N 33/18* (2006.01)

(52) U.S. Cl.
CPC ........... *G01D 11/30* (2013.01); *G01N 33/1886* (2013.01)

(58) Field of Classification Search
CPC ............................ G01D 11/30; G01N 33/1886
See application file for complete search history.

(56) References Cited

U.S. PATENT DOCUMENTS

| 5,106,580 | A | 4/1992 | Mudiam |
| 7,121,158 | B2 | 10/2006 | Scott et al. |
| 2005/0072253 | A1 | 4/2005 | Scott et al. |
| 2006/0065066 | A1* | 3/2006 | Bellis, Jr. ............... G01D 11/30 73/866.5 |
| 2008/0141797 | A1* | 6/2008 | Rodriguez ......... G01N 33/1886 73/866.5 |
| 2012/0125131 | A1* | 5/2012 | Sue ........................ F01D 17/02 73/866.5 |

FOREIGN PATENT DOCUMENTS

EP 1148317 A2 10/2001

OTHER PUBLICATIONS

International Searching Authority (EPO), Search Report for International Application PCT/US2014/057976, Dec. 1, 2014, 3 pages, The Hague, Netherlands.
International Preliminary Report on Patentability for PCT/US2014/057976, Jan. 18, 2016, 12 pages, European Patent Office, Munich, Germany.

* cited by examiner

*Primary Examiner* — David Gray
*Assistant Examiner* — Dennis Hancock
(74) *Attorney, Agent, or Firm* — Ference & Associates LLC

(57) ABSTRACT

Described herein is an insertion mount, including a threaded cylindrical mount with a hollow inner diameter and a lengthwise slot cutout for receiving a probe; and a drive assembly further comprising a drive nut, wherein the drive nut has threads that engage the threaded outer diameter of the threaded cylindrical mount which allows the drive nut to be moved the length of the cylindrical mount by screwing the drive nut of the drive assembly onto the threads of the threaded cylindrical mount.

13 Claims, 14 Drawing Sheets

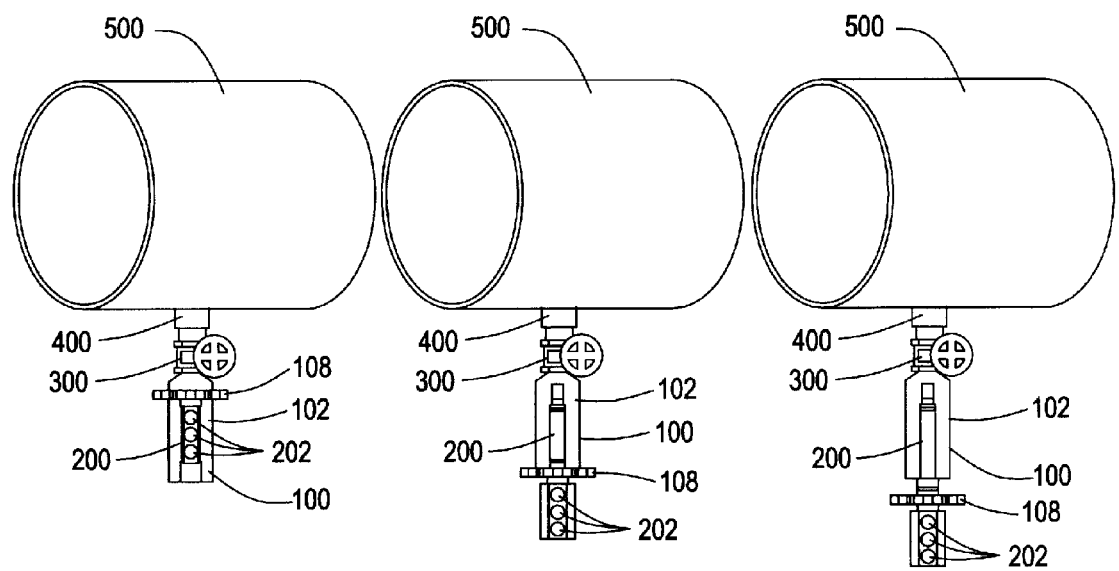

INSERTION MOUNT DEVICE

CLAIM FOR PRIORITY

This application claims priority to U.S. Provisional Application No. 61/885,482 filed on Oct. 1, 2013 entitled "INSERTION MOUNT DEVICE", which is incorporated by reference herein in its entirety.

BACKGROUND

It is often necessary to test liquids in pipes installed in industrial applications. Such testing often uses analytical sensors contained in probes. Generally a test sample must either be removed from the pipe or the probe must be inserted directly into the system pipe. In the former, it may be impractical to remove representative sample from the pipe. In the latter instance, inserting a probe directly into a pipe of a pressurized system, such as a ship ballast system or a municipal drinking water system, it may be necessary to employ hot tapping or similar procedures which involves attaching a branch connection and valve on the outside of an operating pipeline.

In the instance of measuring Total Residual Oxidant (TRO) in ship ballast water as part of a ballast water treatment system to avoid potentially damaging discharges into the environment of a seaport and/or control the ballast water treatment system dosing, certain challenges are presented depending on the ship type and construction of the ballast system. It may be impossible or impractical to drain the ballast pipe or isolate a section of line to remove a probe for maintenance or replacement. Additionally, the ballast pipes in ships are located in areas with limited spaces for access around the pipes. A further complicating factor is that marine environments generally present higher vibrations than many other industrial environments.

While adaptor devices that can insert a probe into a pressurized pipe are known, see, for example, U.S. Pat. No. 7,121,158, two main problems are presented. The length of the adaptor used in such a device often requires too much space around the pipe to use the device. The longer lengths of typical assemblies are necessary however because the probe and whatever mechanism is used to drive it must be pulled completely straight back through the pipe valve while it is still sealed to the outside, allowing the valve to be closed prior to removing the probe from the assembly. Thus the service length (as used herein, the space needed to remove the probe) is equal to at least the length of the valve and adapter assembly and twice the insertion length of the probe. Customers are also unlikely to accept long fittings that project from the pipe for fear of vibration damage to the device or pipe. User safety is another issue impacting the design of such devices with respect to probe insertion or removal from a pressurized pipe. Thus, there is a need for a more optimal service length device for constricted or limited space probe applications.

BRIEF SUMMARY

Broadly contemplated herein, at least one presently preferred embodiment is directed to an insertion mount apparatus for inserting and withdrawing test probes into and out of a system pipe, the insertion mount having a lengthwise slot cutout in its length through which a probe is inserted and removed.

In summary, one embodiment provides an insertion mount, comprising: a threaded cylindrical mount with a hollow inner diameter and a lengthwise slot cutout for receiving a probe; and a drive assembly further comprising a drive nut, wherein the drive nut has threads that engage the threaded outer diameter of the threaded cylindrical mount which allows the drive nut to be moved the length of the cylindrical mount by screwing the drive nut of the drive assembly onto the threads of the threaded cylindrical mount.

Another embodiment provides an insertion mount device with a probe for insertion therein, comprising: a threaded cylindrical mount with a hollow inner diameter and a lengthwise slot cutout for receiving a probe; a drive assembly further comprising a drive nut, wherein the drive nut has threads that engage the threaded outer diameter of the threaded cylindrical mount which allows the drive nut to be moved the length of the cylindrical mount by screwing the drive nut of the drive assembly onto the threads of the threaded cylindrical mount; and a probe capable of insertion and removal from the slot cutout in said threaded cylindrical mount.

For a better understanding of exemplary embodiments together with other and further features thereof, reference is made to the following description, taken in conjunction with the accompanying drawings, and the scope of the claimed embodiments will be pointed out in the appended claims.

BRIEF DESCRIPTION OF THE SEVERAL VIEWS OF THE DRAWINGS

FIGS. 4A-4C show, respectively, perspective views of an insertion mount device in an embodiment with a probe in the inserted position (FIG. 4A), retracted position (FIG. 4B), and service position (FIG. 4C).

DETAILED DESCRIPTION

It will be readily understood that the components of the embodiments, as generally described and illustrated in the figures herein, may be designed in a wide variety of different configurations in addition to the described exemplary embodiments. Thus, the following detailed description of the embodiments, as represented in the figures, is not intended to limit the scope of the claims, but is merely for illustration of certain selected exemplary embodiments as claimed herein.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of the embodiments. One skilled in the relevant art will recognize, however, that the various embodiments can be practiced without one or more of the specific details, or with other methods, components, materials, and so forth. In other instances, well-known structures, materials, or operations are not shown or described in detail to avoid obscuring aspects of the embodiments.

The description now turns to the figures. The illustrated embodiments will be best understood by reference to the figures. The following description is intended only by way of example and simply illustrates certain exemplary embodiments as claimed herein.

Figure 1A:
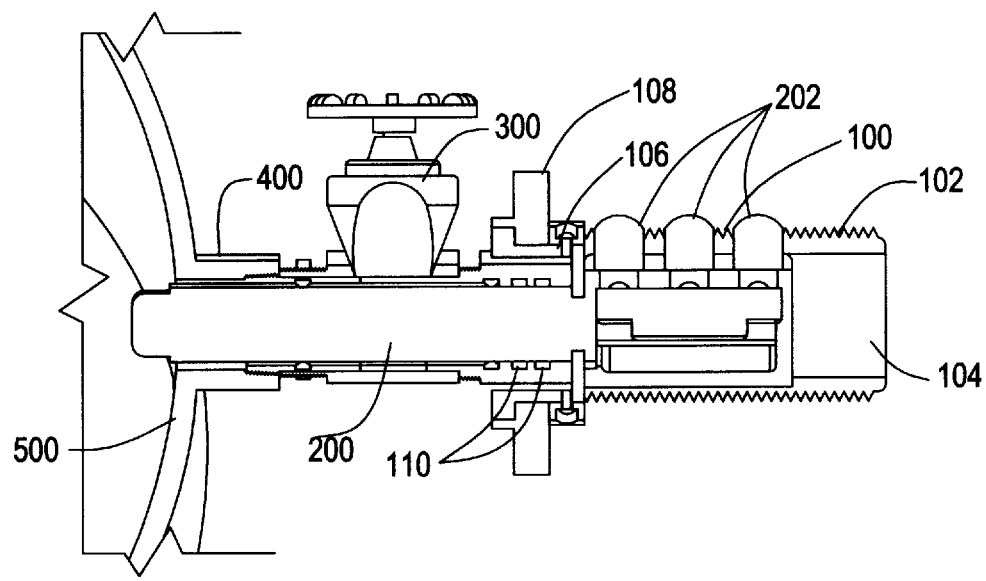
FIGS. 1A and 1B are cutaway side views of an insertion mount with, respectively, a probe in the inserted state (FIG. 1A) and refracted state (FIG. 1B) in an example embodiment.
Figure 1B:
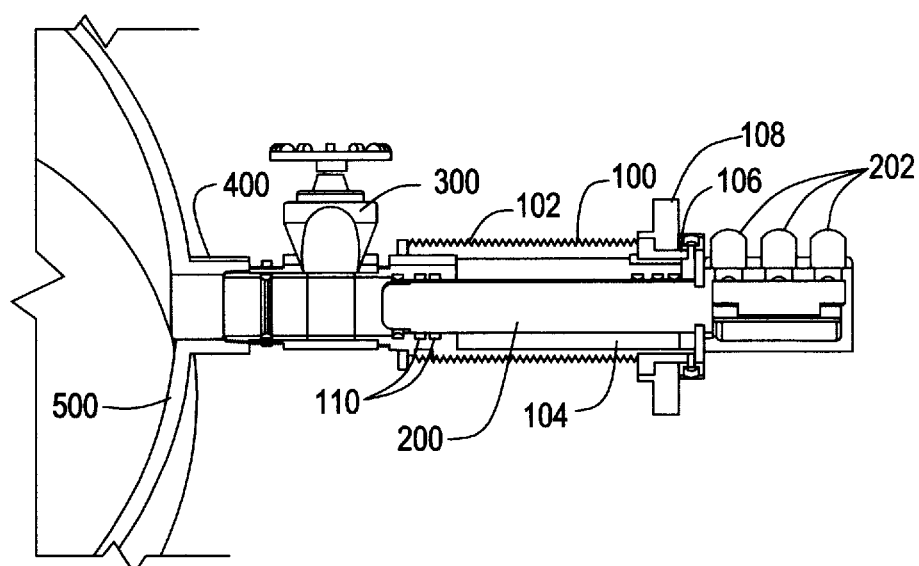

FIGS. 1A and 1B show insertion mount 100 with probe 200 in inserted and refracted states, respectively. Insertion mount 100 is connected to valve 300 (e.g., via complimentary threading as illustrated) which in turn is fitted to branch connection 400 which is ultimately fitted to or forms part of an opening in test pipe 500. Insertion mount 100 includes a threaded cylindrical mount 102 a portion of which has a hollow inner diameter and slot or cutaway 104, which may also be described as similar to a split drive screw (which is hollow) through which probe 200 is installed and removed laterally from the service position state of the probe. Generally the threads of cylindrical mount 102 may run substantially the length of cylindrical mount 102 as shown in FIGS. 1A and 1B.

Drive assembly 106 of insertion mount 100 is configured to include a threaded collar, having threaded drive nut 108, and has mechanism by which probe 200 can be securely attached. The threads of drive nut 108 sit on top of the threads of threaded cylindrical mount 102 which allows drive assembly 106 and attached probe 200 to be moved downward toward valve 300 or upward and outward away from valve 300 by the action of accordingly screwing drive nut 108 axially along threaded cylindrical mount 102. Slot or cutout 104, as seen also in FIG. 3B, is of a width sufficient to accommodate lateral insertion of probe 200 and begins at the end of threaded cylindrical mount 102 furthest from valve 300 and extends substantially the length of cylindrical mount 102. Slot 104 ends at a point before the end of threaded cylindrical mount 102 so as to accommodate seals such as o-rings 110, two rings in this example embodiment. O-rings 110 or similar seals are made of rubber or similar sealing material to form a seal at the valve end of insertion mount 100 to prevent pressurized water or other fluid from pipe 400 from flowing outward over the end of probe 200.

Probe 200 and drive assembly 106 must be seated in threaded cylindrical mount 102 before the valve 300 is opened. In order to insert probe 200 into test pipe 400 probe 200 with attached drive assembly 106 is first inserted laterally through slot 104 of threaded cylindrical mount 102. Probe 200 must next be advanced axially far enough to engage o-rings 110 before valve 300 is opened. Valve 300 is then opened, and the drive assembly 106 and attached probe 200 are then moved axially as a unit toward the opening of test pipe 500 by screwing drive nut 108 down toward the opening of test pipe 500. Communication ports 202 at the end of probe 200 are used for connecting wires, electrodes and the like for communicating data for readouts of the various parameters and conditions of the fluid or water in test pipe 500.

As shown in FIG. 1B, probe 200 has been retracted by screwing drive nut 108 along the shaft of threaded mount 102 away from test pipe 500 and valve 300. Valve 300 is closed after the testing end of the probe clears the valve but is still sealed by the o-rings and the pipe is thereby sealed with the probe 200 in the retracted position. If desired, the probe 200 can then be moved to the service state position by moving it further outward axially until the testing end of the probe clears the valve end of slot 104 and then can be removed laterally from insertion mount 100 for servicing or total removal. Thus this example embodiment shows an extraction arrangement that allows for lateral removal of probes that is space-efficient and by being shorter overall than other apparatuses and is less prone to vibrational damage.

Figure 2:
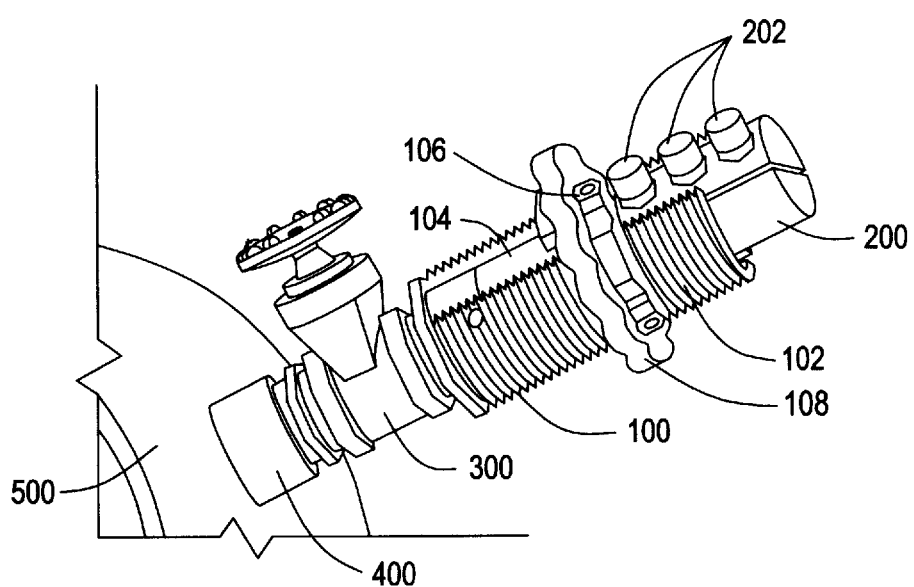
FIG. 2 is a perspective view of an insertion mount with a probe in the halfway inserted position in an example embodiment.

FIG. 2 shows the device of one example embodiment in which probe 200 is inserted halfway into insertion mount 100 after valve 300 has been opened. Probe 200 is securely mounted onto drive assembly 106 and the entire drive assembly and probe combination are positioned in relation to threaded cylindrical mount 102 such that cutaway 104 in threaded cylindrical mount 102 receives probe 200 and drive assembly 106 as it is inserted laterally. In order to attain the probe position shown in FIG. 2, drive nut 108 which is a threaded ring, and which may feature a sprocket design for ease of use, is then positioned over the threads of the threaded cylindrical mount 102 and then screwed downward toward open valve 300 until it is halfway inserted. The thread of the insertion mount described herein operates to hold the position of the insertion mount assembly against pressure trying to push the probe out of test pipe 500, or negative pressure trying to pull the probe into test pipe 500. It also allows the probe to be inserted or retracted against positive pressures.

Figure 3A:
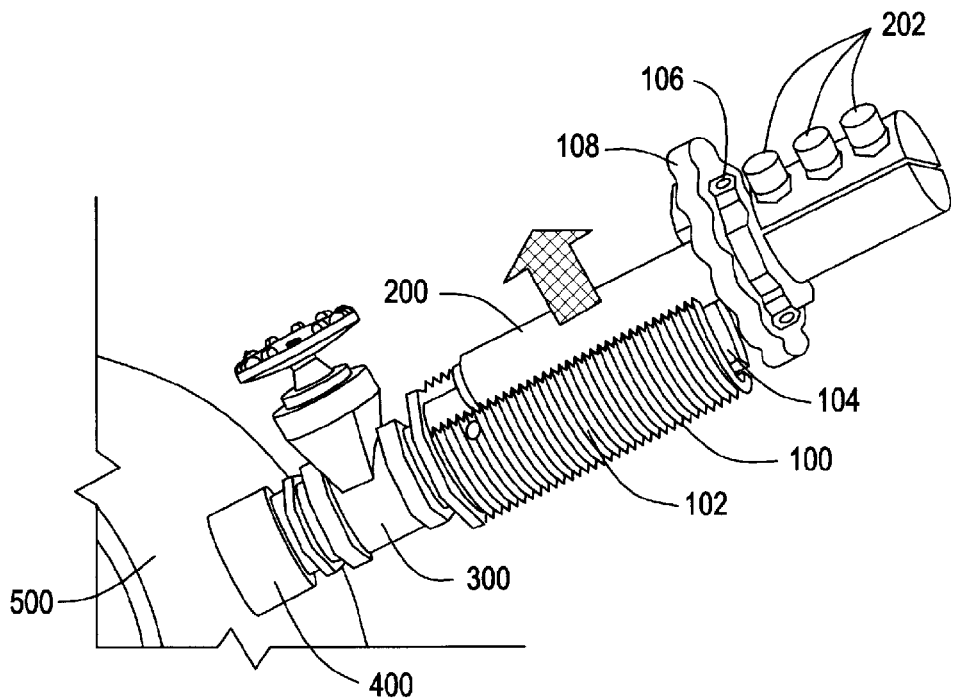
FIG. 3A is a perspective view of an insertion mount where a probe is being removed from the service position in an example embodiment.
Figure 3B:
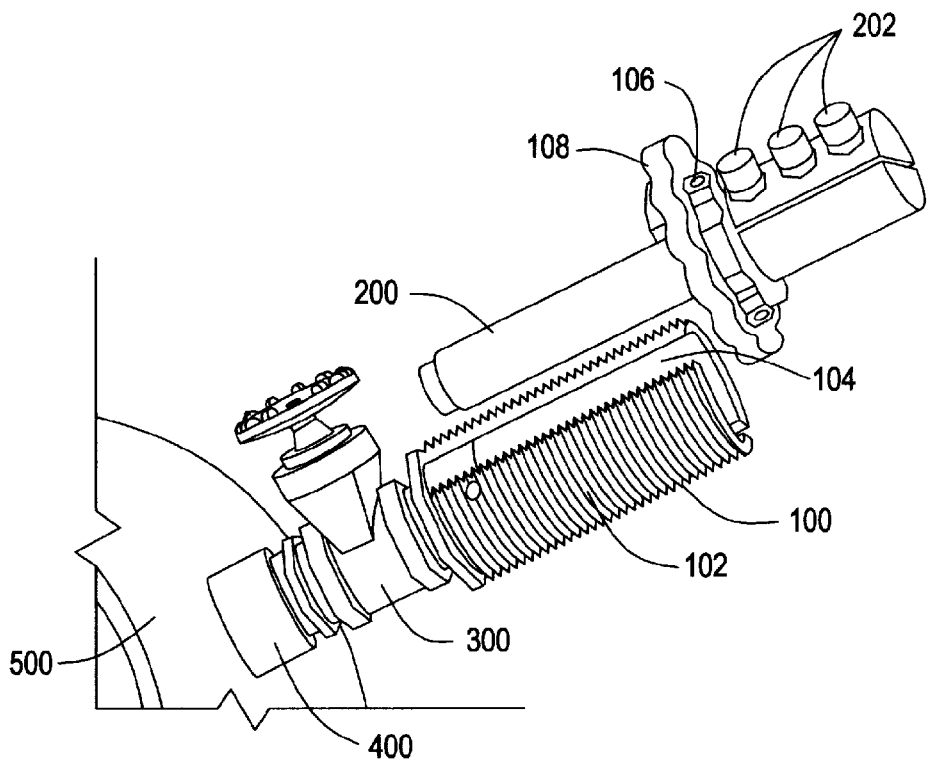
FIG. 3B is a perspective view of an insertion mount where a probe is totally removed from the service position in an example embodiment.

FIGS. 3A and 3B show insertion mount 100 and probe 200 as a further example embodiment in which probe 200 is removed from the service position state of the probe (the space needed to remove the probe), also shown in FIG. 4C. Valve 300 is closed for this operation to prevent water or other liquid from test pipe 500 from forcing itself outward. Probe 200, once in its service position, is moved laterally and outward in the direction of the arrow through slot 104 from the cylindrical cavity of threaded cylindrical mount 102 (FIG. 3A). Drive assembly 106 is attached to probe 200 and threads on an inner circumference of drive nut 108 are placed onto the threads on the outer diameter of threaded cylindrical mount 102. Drive nut 108 is screwed inward (to insert) or outward (to retract) along the length of the threaded cylindrical mount 100. In FIG. 3B the probe 200 is totally removed from the assembly for servicing, analysis, or replacement.

It can be appreciated that lateral removal of probe 200 means that the clearance around test pipe 500 is much less than would normally be the case in other such assemblies because in such cases the probe 200 and whatever mechanism is used to drive or move it through the valve 300 would have to be pulled straight back along the axis of the probe 200 out of a conventional mount, making the service length in such instances equal to at least the length of the valve and housing or mount mechanism, plus the probe length, e.g., twice (or greater than) the insertion length. As seen in FIGS. 3A and 3B removal of probe 200 laterally via cutout 104 in threaded mount 102 allows the service length to be the length of valve 300 and the length of insertion mount 100 lengths. Such an insertion mount 100 and the probe 200 it houses is, as a unit, shorter overall which allows the device to be used in areas with less clearance room around the pipe 500 and additionally to be more durable in that it is less prone to damage from marine or other industrial vibrations.

Probe 200 is configured to measure various characteristics of the fluid in test pipe 500. Probe 200 may measure temperature, pressure, pH, dissolved oxygen, and/or chlorine, as well as other characteristics of the fluid. An example of probe 200 that may be used herein is probe TR3500sc available from Hach Company of Loveland, Colo. USA.

Insertion mount 100 may be made of any suitable material such as, for example, stainless steel, copper, polymers, or other suitable materials given the desired use environment (e.g., marine), the desired drive mechanism, or arrangement (e.g., complementary threading, sliding or pin-locking, etc.).

FIGS. 4A-4C show the length of the insertion mount assembly in the inserted position (FIG. 4A), retracted position (FIG. 4B), and the service position (FIG. 4C) which have been illustrated by means of the previous figures. Due to the side mount arrangement shown herein which allows the probe 200 to be removed laterally through a slot cut out of a threaded cylindrical mount 100, the service position (the valve and insertion mount length), (FIG. 4C) is only slightly longer than the length of the insertion mount assembly in the retracted position (FIG. 4B). Thus the insertion mount assembly of this embodiment can be used in areas which have less working room around the test pipe and/or are subject to potentially damaging vibrations.

Figure 5:
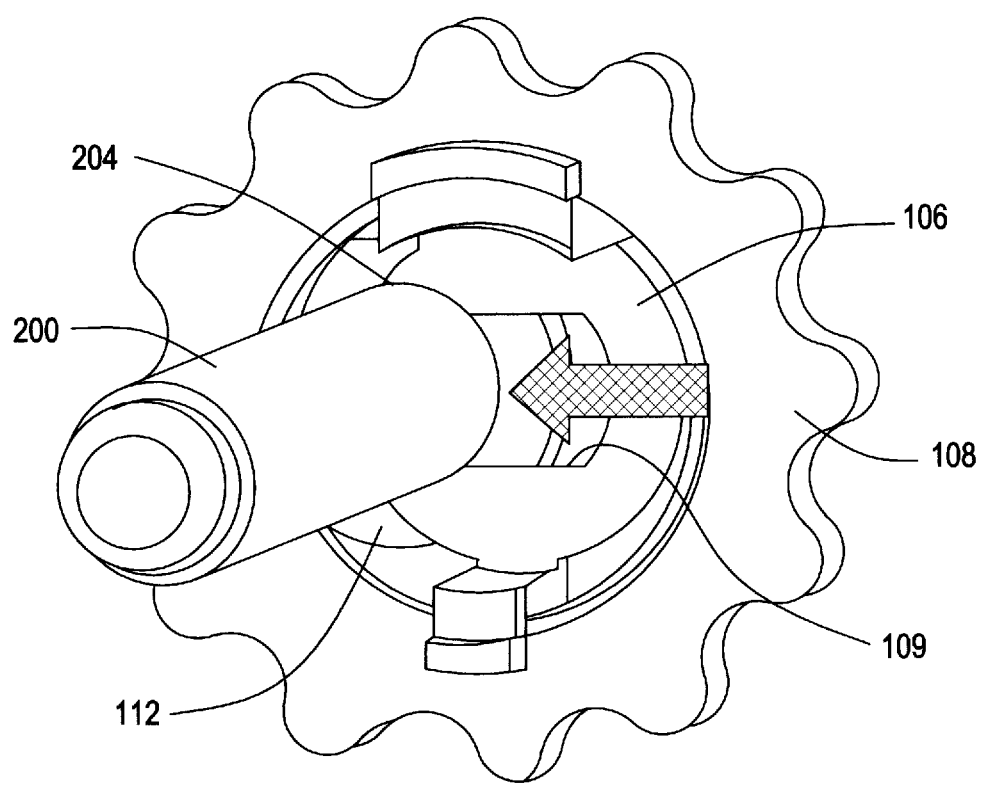
FIG. 5 is a perspective view of a drive assembly with a probe attached thereto that is moved laterally for removal in an example embodiment.

The interface between probe 200 and drive assembly 106 is shown in FIG. 5 by way of example. Drive assembly 106 secures probe 200 via probe slot 109 that is formed in drive assembly 106. Probe slot 109 in drive assembly 106 receives probe 200 by means of a flat section or notch 204 at the top end of probe 200. Probe notch 204 allows probe 200 to slide laterally into probe slot 109 for installation, or when the probe is to be removed from the drive assembly, it is slid out of the probe slot 109 as indicated by the arrow in FIG. 5. While the probe 200 is fully inserted into test pipe 500 as described hereinabove, the probe 200 cannot slide laterally and is held on axis due to this assembly.

In addition to the notch/slot arrangement described above, any other means for affixing probe 200 to drive assembly 106 may be used, for example, a suitable adhesive, clips, or more permanent arrangements such as screws or the like.

Figure 6A:
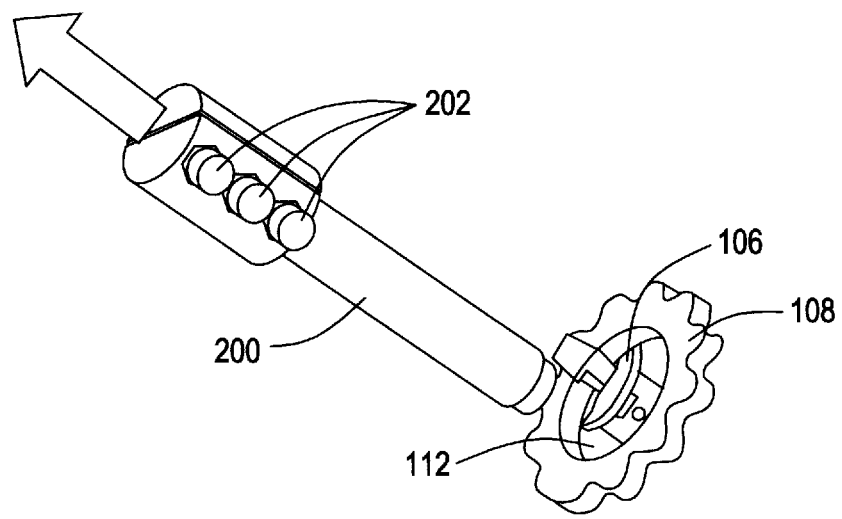
FIG. 6A is a perspective view of a probe being removed from a drive assembly in an example embodiment.

As shown in FIG. 6A, after probe 200 is slid off axis and out of probe slot 109 as shown in FIG. 5, opening 112 in one side of drive assembly 106 allows probe 200 to be removed from the drive assembly 106 by sliding it rearward as shown by the arrow.

Figure 6B:
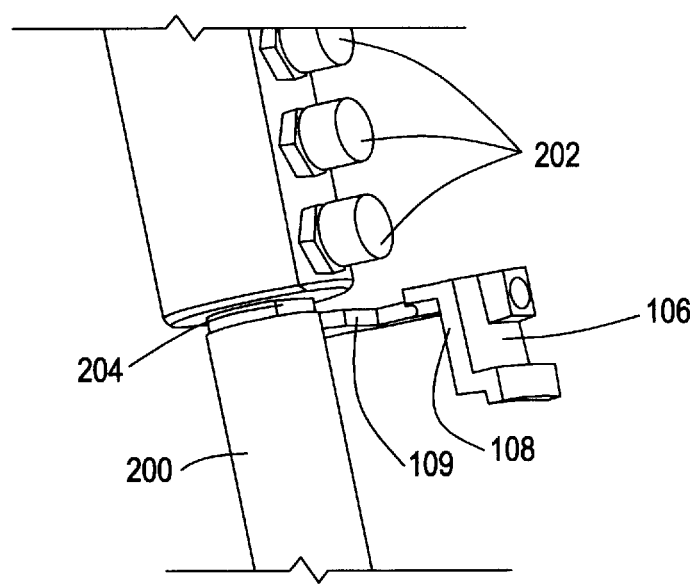
FIG. 6B is a perspective view of the end of a probe with a cutaway partial perspective view of a drive assembly.

FIG. 6B shows further detail of how probe 200 is held in place by drive assembly 106 (only a portion thereof is illustrated). Flat section/notch 204 at an end of probe 200, e.g., proximate to the communication ports 202, allows the drive assembly 106 to control the orientation of the probe 200 in that the probe 200 cannot rotate about its axis once in the drive assembly 106 and the drive. Drive assembly 106 can also push or pull on the probe 200 (adhere to it) by mating with the shoulders created by the flat notches 204 included on the probe 200 in an example embodiment.

In another example embodiment, FIGS. 7-14 generally illustrate safety locking feature(s) for the insertion mount discussed hereinabove. Note that in these figures, the ball or gate of the valve is not shown, due to a simplified computer aided design model.

Figure 7:
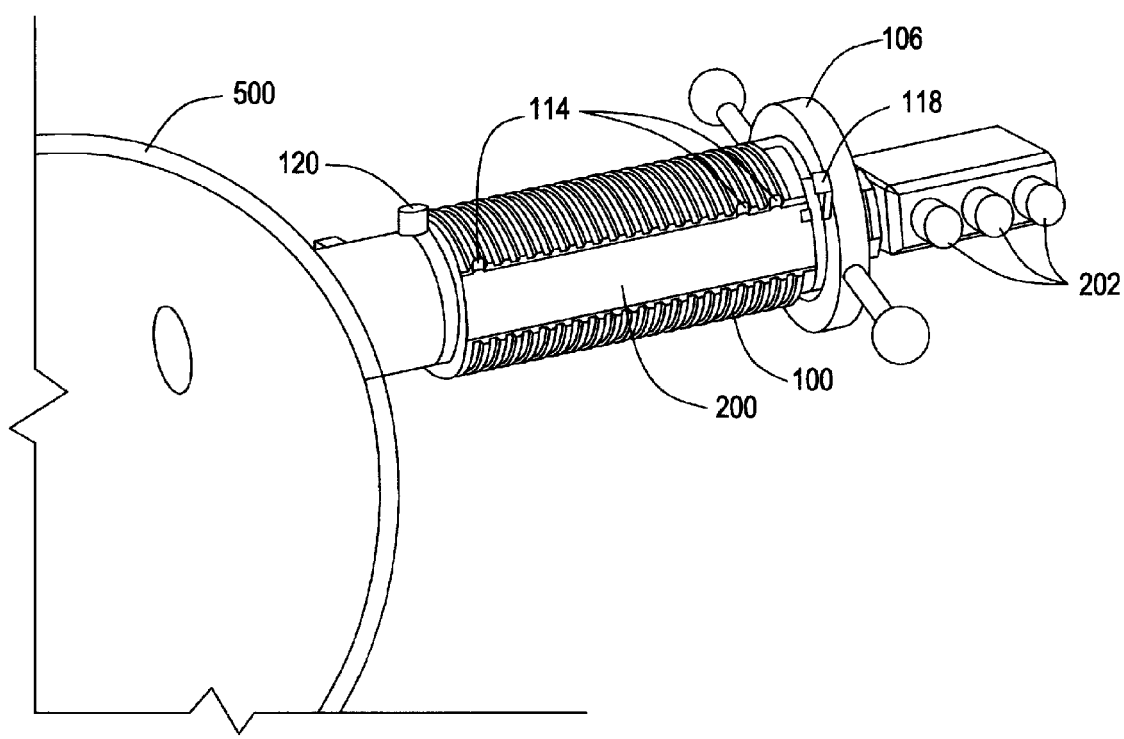
FIG. 7 is a perspective view of an insertion mount in the service position in an example embodiment.

FIG. 7 shows insertion mount 100 in the service position. Three position notches 114 are shown on threaded cylindrical mount 102. In this position, probe 200 can either be removed from the insertion mount assembly, or be positioned to be inserted into the mount assembly, but is not yet connected. Locking tab 118 (which may secure into one of notches 114) is shown as well as vent valve port 120.

Figure 8:
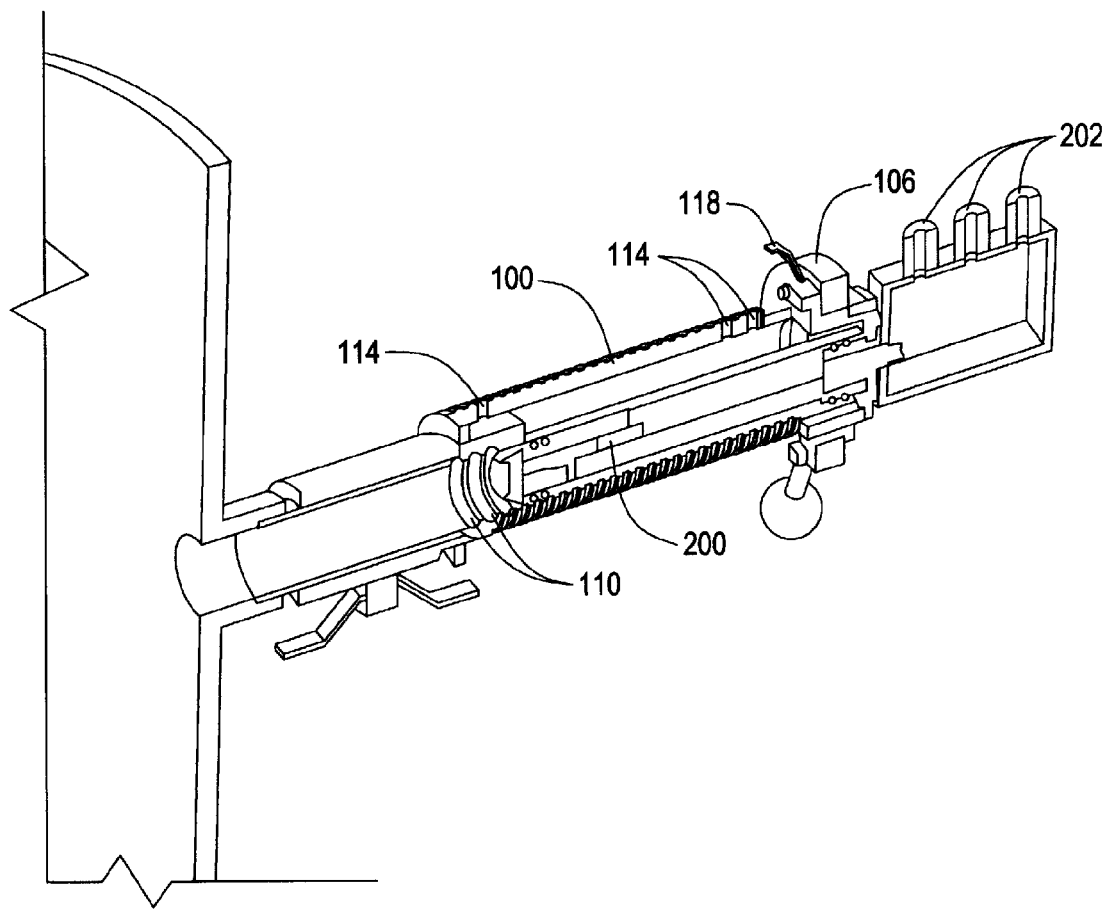
FIG. 8 is a cutaway perspective view of an insertion mount in the service position in an example embodiment.

FIG. 8 shows the same assembly as in FIG. 7, but in a cutaway view. The (measurement) end of probe (proximate to the pipe or conduit) is just entering the valve assembly, but is not yet engaging seals 110 or the sealing surface of the probe. In this embodiment example, the valve and seal assembly are integral.

Figure 9:
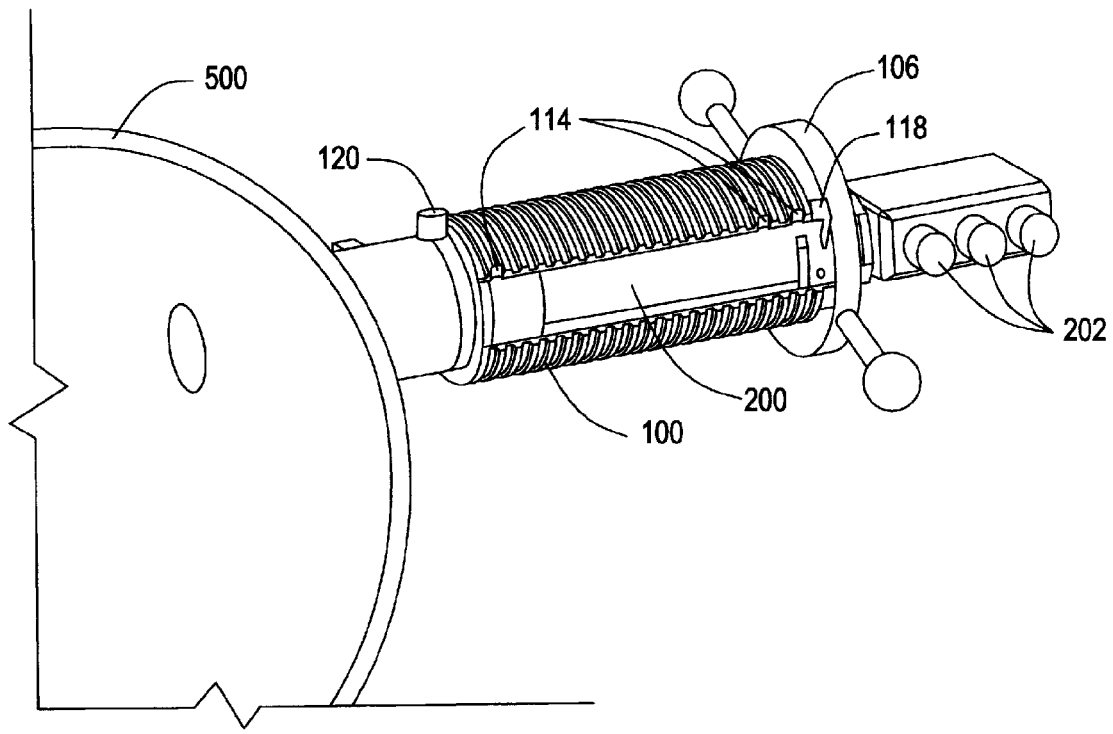
FIG. 9 is a perspective view of an insertion mount in the safety position in an example embodiment.

In FIG. 9, probe is at the first position notch 114. Drive nut 106 is nested on the unthreaded end of insertion mount 100, and locking tab 118 is engaged in first position notch 114. At this position, the probe and drive assembly unit is locked to the insertion assembly by virtue of locking tab 118 (which may be biased, e.g., spring loaded) in notch 114, and the locking tab 118 secures or prevents probe from coming out of the assembly mount 100 unless the locking tab 118 is disengaged form the notch 114, e.g., actuated by pushing it in.

Figure 10:
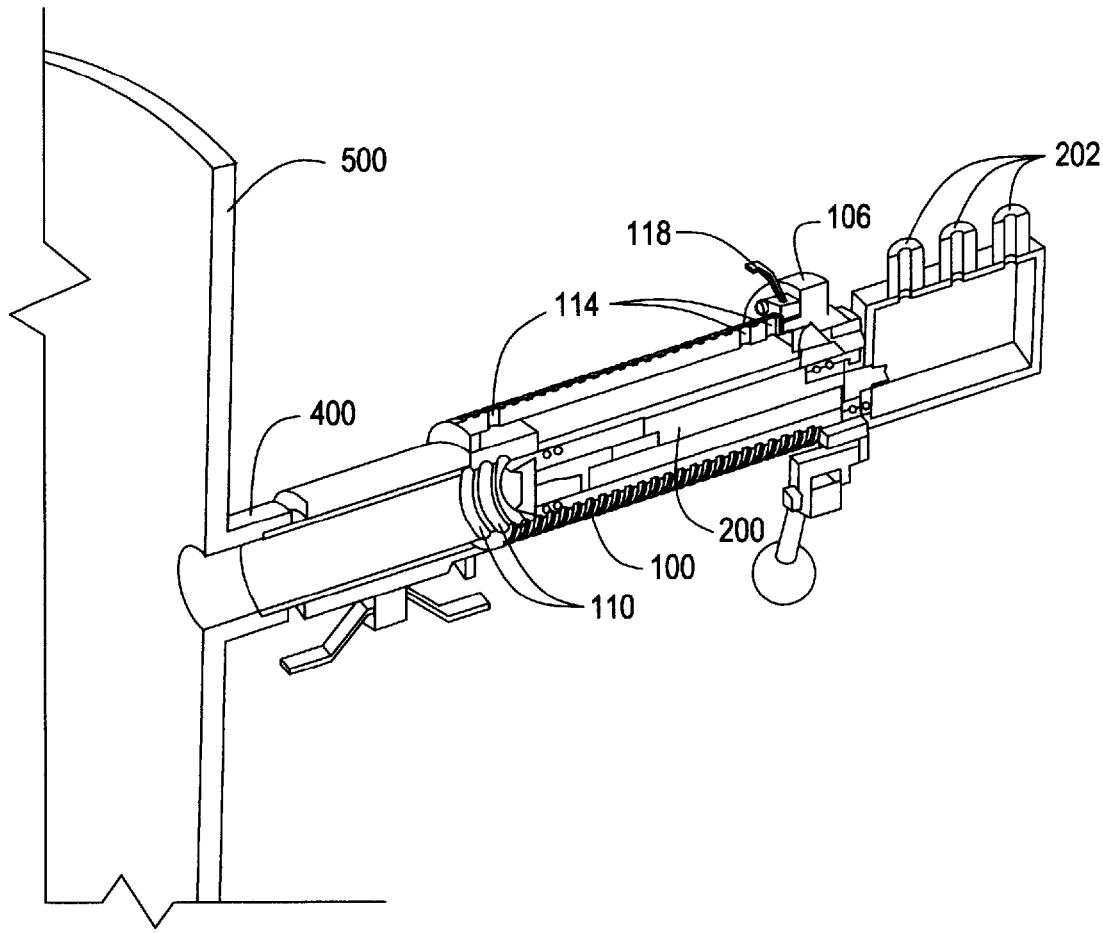
FIG. 10 is a cutaway perspective view of an insertion mount in the safety position in an example embodiment.

In FIG. 10 there is shown a cutaway view of the insertion mount 100 assembly at the safety position. In this position, the probe 200 and drive assembly is captive, but the seals are not yet engaged. The probe end mostly plugs the end of the valve (by virtue of contacting seals 110), so if the valve were opened at this position and there were pressure in the pipe, it may leak significantly, alerting the operator to the open valve condition, while still preventing the probe 200 from being ejected by the pressure in the pipe.

Figure 11:
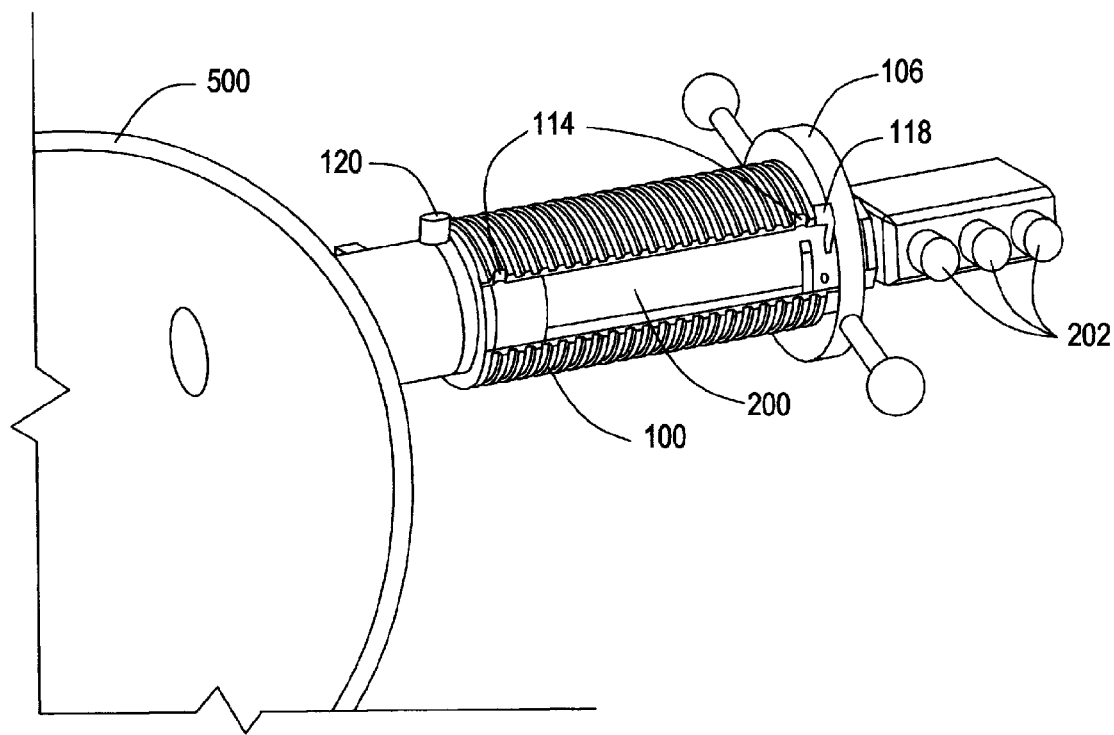
FIG. 11 is a perspective view of an insertion mount in the retracted position in an example embodiment.

FIG. 11 shows probe 200 at the retracted position. Drive 106 is now engaged on the threads of threaded cylindrical mount 100, and locking tab 118 is engaged in second position notch 114. This is the position where the user would normally open the valve prior to moving probe to the inserted position. The probe is engaged with both seals 110 at this point (not shown).

Figure 12:
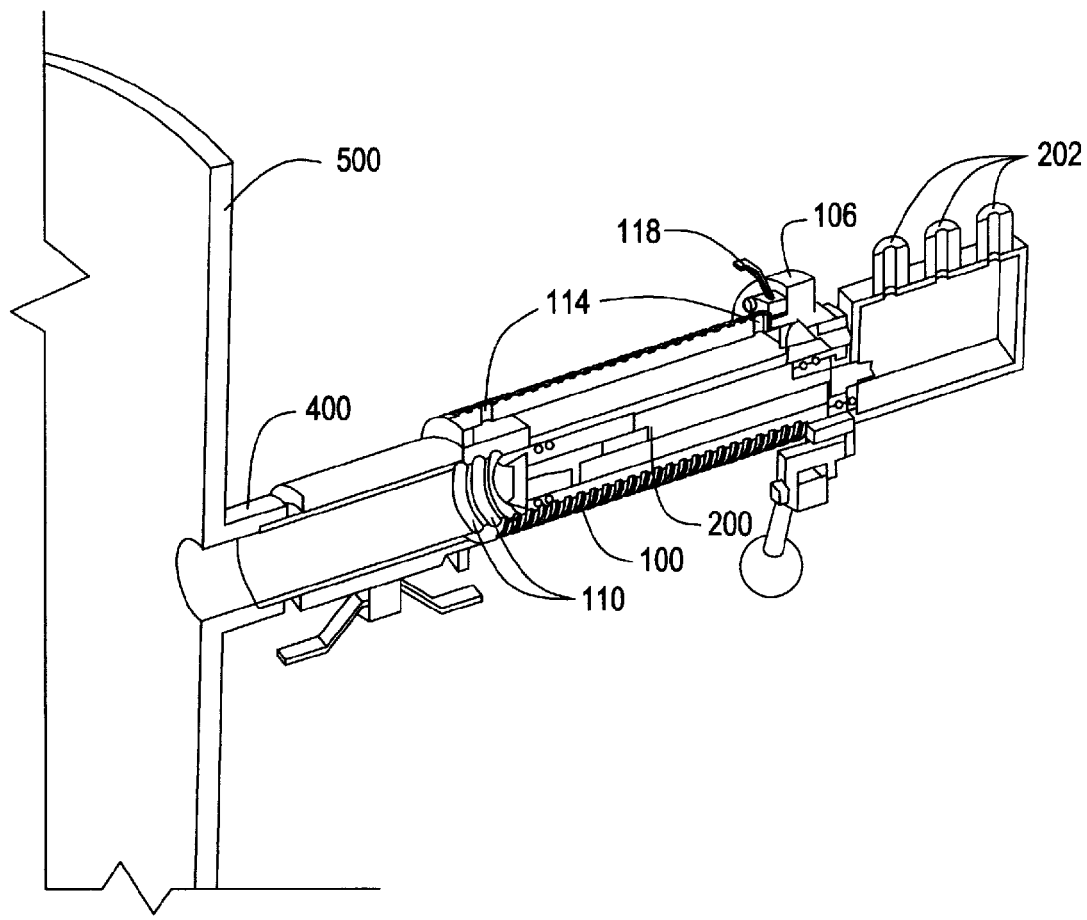
FIG. 12 is a cutaway perspective view of an insertion mount in the retracted position in an example embodiment.

A cutaway view of probe 200 at the retracted position is shown in FIG. 12. As seen in the figure probe 200 is engaged with both seals 110. At this position, the valve can be opened or closed, and the sealing of the insertion mount 100 assembly to the probe 200 prevents leaks.

Figure 13:
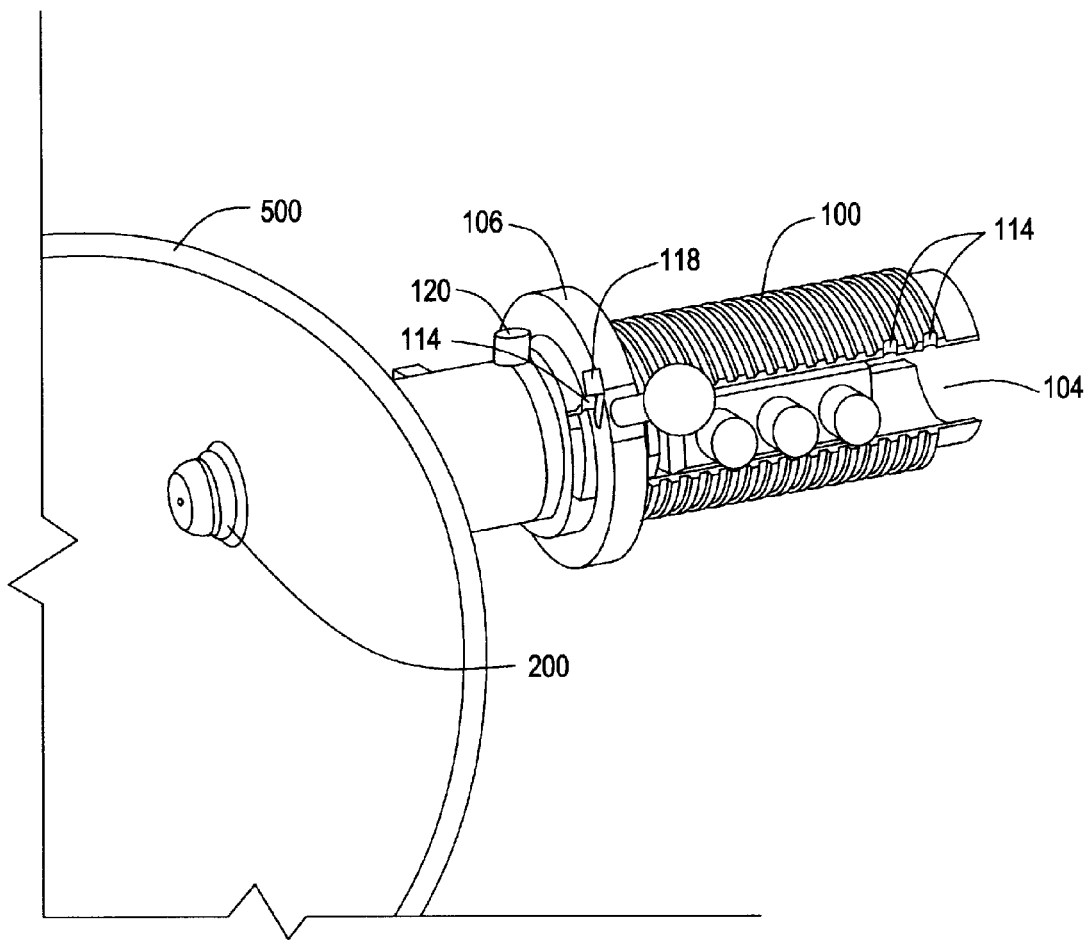
FIG. 13 is a perspective view of an insertion mount in the fully inserted position in an example embodiment.
Figure 14:
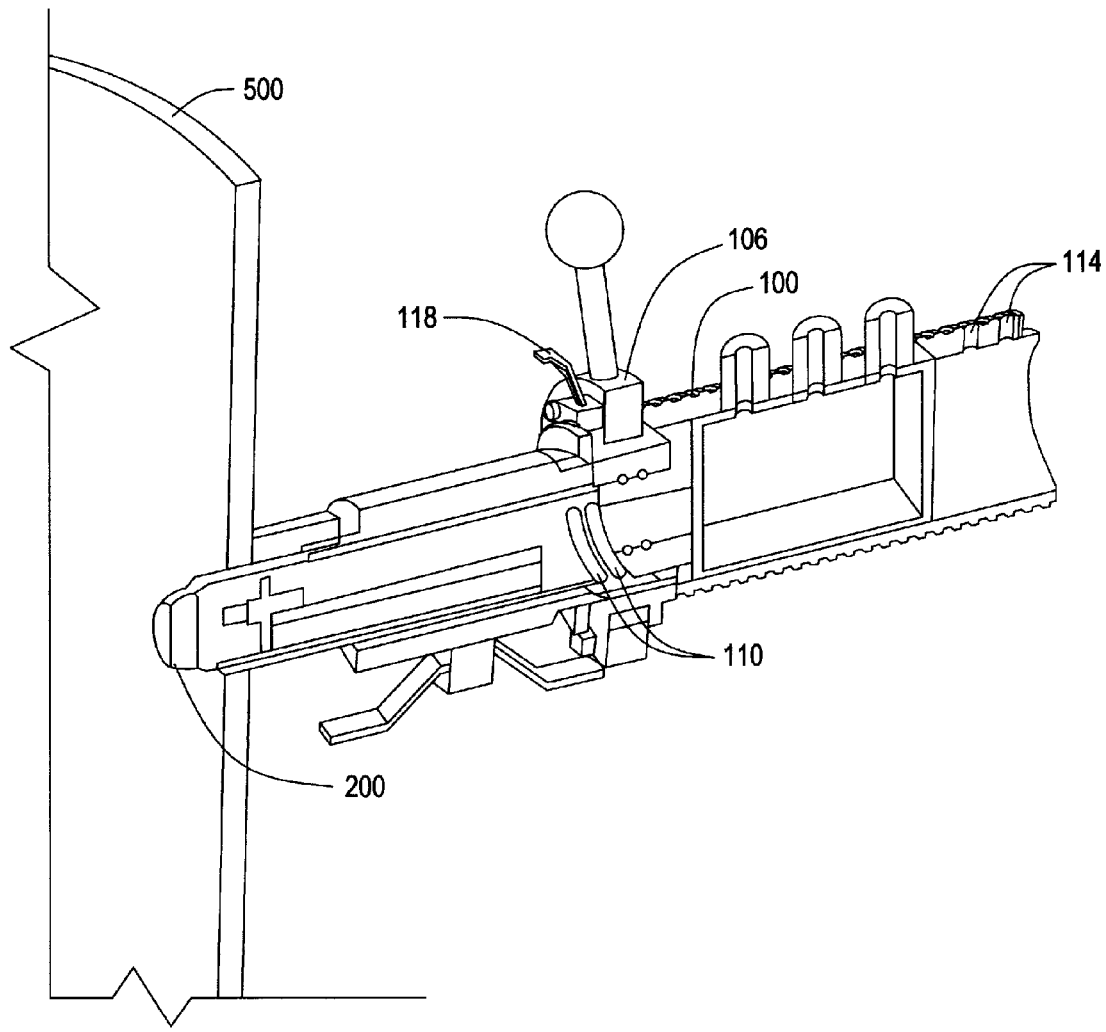
FIG. 14 is a cutaway perspective view of an insertion mount in the fully inserted position in an example embodiment.

FIG. 13 shows the insertion mount assembly 100 in the fully inserted position. Locking tab 118 is engaged in the third, final position notch 114, preventing the probe 200 from backing out due to vibration or other reasons, and is a signal to the operator that the mount assembly is at the fully inserted position. At this position, the probe sensor is inserted into the process through the open valve and into test pipe. In FIG. 14 there is shown a cutaway view of the mount assembly 100 with probe 200 in the fully inserted position through the seals 110 and the valve.

Vent valve port 120 (FIG. 7) in an example embodiment operates such that when probe 200 is sealed in the retracted position with the main valve closed, the probe 200 would be hydraulically locked into the insertion mount assembly unless the vent valve is opened to allow air in.

The safety features shown in FIGS. 7-14 and described above, operate in an insertion workflow as follows. Probe 200 and attached drive assembly 106 are seated onto the unthreaded portion of threaded cylindrical insertion mount 102, and pushed into it until locking tab 118 clicks into place in first position notch 114—the safety position. The operator then verifies that vent valve 120 is open. The operator then moves (e.g., uses drive nut 108) to engage the threads of the cylindrical mount and presses locking tab 118 to allow the insertion mount assembly to move to the next (second) position, and then turns the drive nut 108 until locking tab 108 clicks into the second position notch 114—the retracted position. Vent valve 120 is then closed. The operator then opens the main valve, pushes locking tab 118 to allow the insertion mount assembly to move to the next (third) position, and uses the drive nut 108 to drive the probe 200 fully into the test process, until locking tab 118 engages in the final (third) position notch 114 for the fully inserted position.

The safety features shown in FIGS. 7-14 and described above, operate in a refraction workflow as follows. The operator actuates locking tab 118 and uses drive nut 108 to pull the probe out of the test process, retracting it until locking tab 118 engages in the retracted (second) position notch 114. The operator closes the main valve, opens vent valve 120, and actuates locking tab 118 to allow the operator to unthread drive nut 108 until locking tab 118 engages in the safety position at first position notch 114. The operator then actuates locking tab 118 and disengages the probe/drive assembly and removes it from the insertion mount. As an exception to the foregoing, if during retraction, the operator forgets to close the main valve and tries to remove the probe 200, the seals will disengage as the probe travels from the retracted (second) position notch to the safety (first) position notch, and will start to leak considerably, signaling the user that the valve is still open. A safety latch will engage in first position notch 114 and prevent the probe from being ejected from the assembly. The user would then close the valve and continue as normal.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Although illustrative embodiments have been described herein with reference to the accompanying drawings, it is to be understood that the embodiments are not limited to those particular descriptions, and that various other changes and modifications may be affected therein by one skilled in the art without departing from the scope or spirit of the disclosure.

What is claimed is:

1. An insertion mount, comprising:
   a threaded cylindrical mount with a hollow inner diameter and a lengthwise slot cutout of width sufficient to accommodate lateral insertion of a probe; and
   a drive assembly attachable to the probe prior to lateral insertion of the probe in the threaded cylindrical mount, the drive assembly having an opening for fitting of the probe therein and a slot that mates with a notch of the probe, the drive assembly further comprising a drive nut, wherein said drive nut has threads that engage the threaded outer diameter of said threaded cylindrical mount which allows said drive nut to be moved the length of said cylindrical mount by screwing the drive nut of said drive assembly onto the threads of said threaded cylindrical mount.

2. The insertion mount of claim 1, wherein said lengthwise cutout in said threaded cylindrical mount extends substantially the length of said threaded cylindrical mount.

3. The insertion mount of claim 1, wherein said threaded cylindrical mount has seals adjacent the end of said lengthwise cutout.

4. The insertion mount of claim 3, wherein said seals comprises at least one o-ring.

5. The insertion mount of claim 1, wherein the end of said threaded cylindrical mount adjacent the end of said lengthwise cutout can be secured to a valve.

6. The insertion mount of claim 1, wherein said drive assembly secures a probe therein.

7. An insertion mount device with a probe for insertion therein, comprising:
   a threaded cylindrical mount with a hollow inner diameter and a lengthwise cutout of width sufficient to accommodate lateral insertion of a probe;
   a drive assembly attachable to the probe prior to lateral insertion of the probe in the threaded cylindrical mount, the drive assembly having an opening for fitting of the probe therein and a slot that mates with a notch of the probe, the drive assembly further comprising a drive nut, wherein said drive nut has threads that engage the threaded outer diameter of said threaded cylindrical mount which allows said drive nut to be moved the length of said cylindrical mount by screwing the drive nut of said drive assembly onto the threads of said threaded cylindrical mount; and
   a probe capable of insertion and removal from said slot lengthwise cutout in said threaded cylindrical mount.

8. The insertion mount of claim 7, wherein said lengthwise cutout in said threaded cylindrical mount extends substantially the length of said threaded cylindrical mount.

9. The insertion mount of claim 7, wherein said threaded cylindrical mount has seals adjacent the end of said lengthwise cutout.

10. The insertion mount of claim 9, wherein said seals comprises at least one o-ring.

11. The insertion mount of claim 7, wherein the end of said cylindrical mount adjacent the end of said lengthwise cutout can be secured to a valve.

12. The insertion mount of claim 7, wherein said drive assembly secures said probe.

13. A kit, comprising,
   an insertion mount, comprising:
      a threaded cylindrical mount with a hollow inner diameter and a lengthwise slot cutout of width sufficient to accommodate lateral insertion of a probe; and
      a drive assembly attachable to the probe prior to lateral insertion of the probe in the threaded cylindrical mount, the drive assembly having an opening for fitting of the probe therein and a slot that mates with a notch of the probe, the drive assembly further comprising a drive nut, wherein said drive nut has threads that engage the threaded outer diameter of said threaded cylindrical mount which allows said drive nut to be moved the length of said cylindrical mount by screwing the drive nut of said drive assembly onto the threads of said threaded cylindrical mount, and a probe that can be inserted and removed from said lengthwise cutout of said threaded cylindrical mount.

* * * * *